US00PP18325P2

(12) United States Plant Patent
Schräder

(10) Patent No.: US PP18,325 P2
(45) Date of Patent: Dec. 18, 2007

(54) **NEW GUINEA *IMPATIENS* PLANT NAMED 'GRÜNEU 23'**

(50) Latin Name: *Impatiens hawkeri*
Varietal Denomination: GrüNeu 23

(75) Inventor: Ralf Schräder, Lüdinghausen (DE)

(73) Assignee: Gruenewald Veredelings B.V., MN's-Gravenzande (NL)

( * ) Notice: Subject to any disclaimer, the term of this patent is extended or adjusted under 35 U.S.C. 154(b) by 0 days.

(21) Appl. No.: 11/480,098

(22) Filed: Jun. 30, 2006

(51) Int. Cl.
*A01H 5/00* (2006.01)

(52) U.S. Cl. ..... Plt./318

(58) Field of Classification Search ..... Plt./318
See application file for complete search history.

*Primary Examiner*—Kent Bell
*Assistant Examiner*—S. B. McCormick-Ewoldt
(74) *Attorney, Agent, or Firm*—The Webb Law Firm

(57) ABSTRACT

'GrüNeu 23' is a new variety of New Guinea *Impatiens* that exhibits violet-pink colored flowers.

1 Drawing Sheet

Botanical classification: *Impatiens hawkeri.*
Varietal denomination: 'GrüNeu 23'.

BACKGROUND OF THE INVENTION

The present invention comprises a new and distinct cultivar of *Impatiens hawkeri* known by the varietal name 'GrüNeu 23'. The new variety was discovered in The Netherlands. The new variety is a result of cross breeding Seedling #1-27 (female parent) (unpatented) and Seedling #2-07 (male parent) (unpatented). The purpose of the breeding program was to develop a cultivar that exhibited large flowers. The new variety is similar in flower color to its parents, but differs in growing habit and flower size. The new variety was first asexually reproduced by vegetative propagation by cutting in The Netherlands. The new variety has been trial and field tested and has been found to retain its distinctive characteristics and remain true to type through successive asexual propagations. Characteristics that distinguish the new variety from others known to the breeder include:

Flower color;

Growing habit; and

Flower size.

The new variety was grown in a 11–21 cm container in The Netherlands. The new variety initiates roots in 8 days at 16° C. A rooted plant is produced in 21 days at average temperatures of 16–21° C. Its rooting habit is round and freely branching.

DESCRIPTION OF THE DRAWING

The accompanying photographic drawing illustrates the new variety, with the color being as nearly true as is possible with color illustrations of this type.

DESCRIPTION OF THE PLANT

Figure 1:
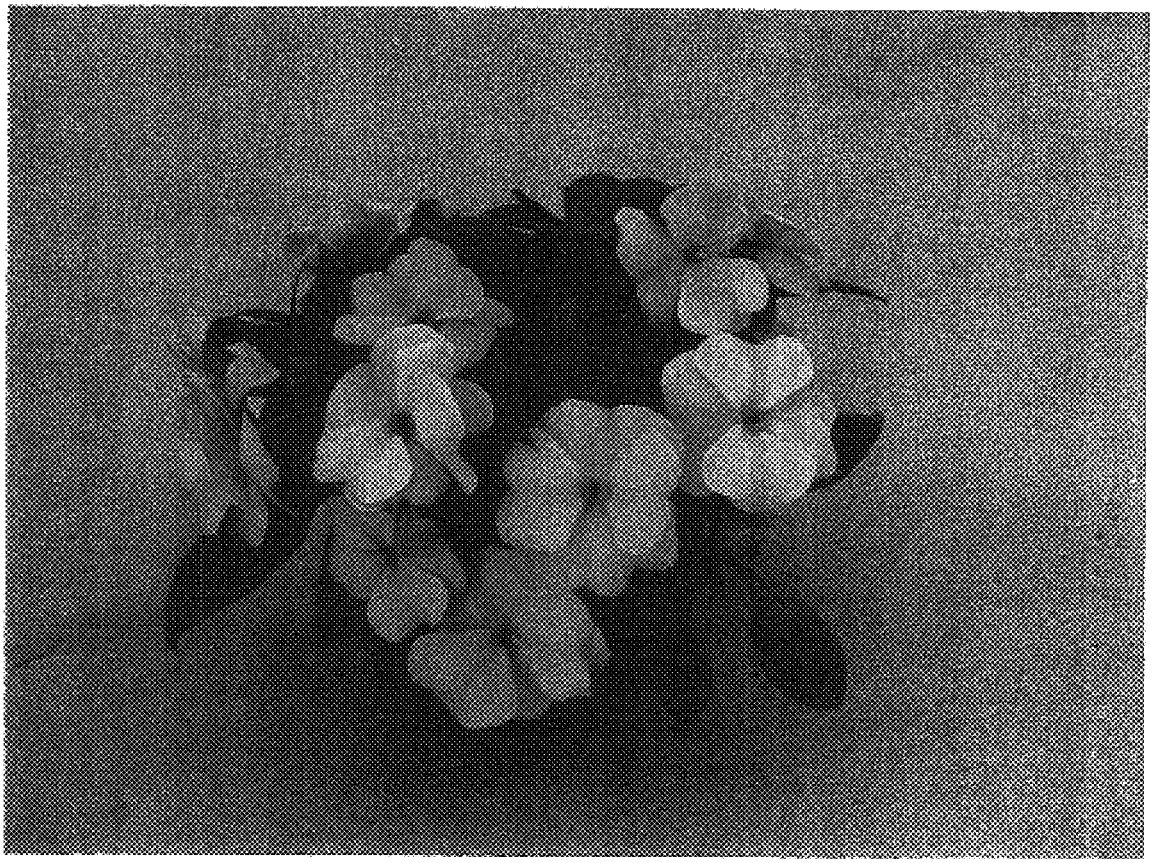

The following detailed description sets forth the characteristics of the new cultivar. The data which defines these characteristics were collected by asexual reproductions carried out in The Netherlands. The color readings were taken indoors in a greenhouse on a sunny day. The new variety was sixteen weeks old from rooting and fully flowering when described. Color references are primarily to The R.H.S. Colour Chart of The Royal Horticultural Society of London (2001).

PLANT

Form: Free and symmetrical.
Height (from soil to top of flowers): 16–19.5 cm.
Plant diameter: 28–32 cm.
Vigor: Upright.
Branching habit: Free.
Lateral branches:
- *Color.*—60A.
- *Texture.*—Smooth.
- *Length.*—15–18 cm.
- *Diameter.*—4–10 mm.
- *Internode length.*—1.3–2 cm.
- *Strength.*—Strong.
- *Quantity.*—14–17.

Foliage:
- *Arrangement.*—Primarily in whorls.
- *Number of leaves per stem.*—10–12.
- *Size of leaf.*—Length: 8.5 cm. Width: 3.6 cm.
- *Shape of leaf (generally).*—Lanceolate.
- *Shape of apex.*—Caudate and acuminate.
- *Shape of base.*—Acute.
- *Texture.*—Glabrous.
- *Aspect.*—Upward and outward.
- *Margin type.*—Slightly serrated.
- *Fragrance.*—None.
- *Color.*—Young leaves: Upper surface: 135B. Lower surface: 176B. Mature leaves: Upper surface: N135B. Lower surface: 176B.
- *Petiole.*—Length: 6–8 mm. Diameter: 2.5 mm. Color: 60A. Texture: Glabrous.
- *Veins.*—Color: Upper surface: 141A. Lower surface: 60B.

FLOWER

Natural flowering season at specified locations: Usually from March to October, depending on light intensity.

Flower type and habit: Single.
Number of flowers per plant: 20–24.
Fragrance: None.
Flower height: 5–10 mm.
Flower diameter: 80 mm.
Bud:
*Shape.*—Ovoid.
*Diameter.*—10 mm.
*Length.*—20 mm.
*Color.*—46A.
Petals:
*Arrangement.*—Whorl.
*Quantity.*—5.
*Length.*—Banner petal: 35 mm. Lateral: 35 mm. Base: 35 mm.
*Width.*—Banner petal: 50 mm. Lateral: 45 mm. Base: 45 mm.
*Shape.*—Cordate.
*Apex.*—Rotundate.
*Base.*—Cuneate.
*Margin.*—Entire.
*Texture.*—Smooth and glabrous.
*Color.*—When opening: Banner, base and lateral petals: Upper surface: 73C. Lower surface: 73D. Fully opened: Banner, base and lateral petals: Upper surface: 73C. Lower surface: 73D.
Spur:
*Quantity.*—1.
*Length.*—50 mm.
*Diameter at apex.*—0.5–1 mm.
*Diameter at flower.*—2 mm.
*Aspect.*—Round.
*Color.*—60B.
Peduncles:
*Length.*—4.7 cm.
*Diameter.*—2.8 mm.
*Color.*—176C.
*Texture.*—Glabrous.
*Orientation.*—Upright.
*Strength.*—Average.
Weather tolerance: +5–+45° C.
Lasting quality:
*On plant.*—3–4 days.
*Of cut flowers.*—1 day.
Seed production and description: Not applicable.
Fruit production and description: Not applicable.

REPRODUCTIVE ORGANS

Stamens:
*Number* (*per flower*).—1.
*Filament length.*—6–8 mm.
*Anthers.*—Shape: Round. Length: 3–4 mm. Color: 58A.
*pollen.*—Color: 69A/B. Amount: Average.
Pistils:
*Length.*—6–7 mm.
*Styles.*—Length: 1–2 mm. Color: 60B.
*Stigma.*—Shape: Round. Color: 60C. Ovary color: 60A.

I claim:

1. A new and distinct variety of New Guinea *Impatiens* plant named 'GrüNeu 23' as is herein described and illustrated.

* * * * *

UNITED STATES PATENT AND TRADEMARK OFFICE

CERTIFICATE OF CORRECTION

PATENT NO. : PP 18,325 P2
APPLICATION NO. : 11/480098
DATED : December 18, 2007
INVENTOR(S) : Schräeder It is certified that error appears in the above-identified patent and that said Letters Patent is hereby corrected as shown below:

Title Page, See Item (75) Inventor, "Ralf Schräder" should read -- Ralf Schräeder --

Signed and Sealed this

Seventeenth Day of June, 2008

JON W. DUDAS
*Director of the United States Patent and Trademark Office*